(12) United States Patent
Shimono et al.

(10) Patent No.: US 10,660,507 B2
(45) Date of Patent: May 26, 2020

(54) IMAGING MODULE AND CATHETER WITH FLEXIBLE WIRING SUBSTRATE

(71) Applicant: FUJIKURA LTD., Tokyo (JP)

(72) Inventors: Takahiro Shimono, Sakura (JP); Hideo Shiratani, Sakura (JP); Kenichi Ishibashi, Sakura (JP)

(73) Assignee: FUJIKURA LTD., Tokyo (JP)

( * ) Notice: Subject to any disclaimer, the term of this patent is extended or adjusted under 35 U.S.C. 154(b) by 383 days.

(21) Appl. No.: 15/058,350

(22) Filed: Mar. 2, 2016

(65) Prior Publication Data

US 2016/0296102 A1   Oct. 13, 2016

(30) Foreign Application Priority Data

Apr. 9, 2015   (JP) ................................. 2015-080227

(51) Int. Cl.
*A61B 1/05* (2006.01)
*A61B 1/00* (2006.01)
(Continued)

(52) U.S. Cl.
CPC ...... *A61B 1/00114* (2013.01); *A61B 1/00096* (2013.01); *A61B 1/05* (2013.01);
(Continued)

(58) Field of Classification Search
CPC ....... A61B 1/041; A61B 1/0114; A61B 1/051; A61B 1/04; A61B 1/05; A61B 1/00096;
(Continued)

(56) References Cited

U.S. PATENT DOCUMENTS 5,220,198 A * 6/1993 Tsuji ........................ A61B 1/05
257/680
5,506,401 A * 4/1996 Segawa ............. H01L 27/14618
250/208.1
(Continued)

FOREIGN PATENT DOCUMENTS

EP   2 677 736 A1   12/2013
JP   2007-330706 A   12/2007
(Continued)

OTHER PUBLICATIONS

Communication, dated Jun. 7, 2016, from the Japanese Patent Office in counterpart Japanese application No. 2015-080227.
(Continued)

*Primary Examiner* — Timothy J Neal
*Assistant Examiner* — William B Chou
(74) *Attorney, Agent, or Firm* — Sughrue Mion, PLLC

(57) ABSTRACT

An imaging module includes an electrical cable; a solid-state imaging element having an imaging unit orthogonal to an axis direction of a tip of the electrical cable; and a flexible wiring substrate in which the solid-state imaging element and the electrical cables are electrically connected together. The flexible wiring substrate includes an element mounting portion mounting the solid-state imaging element, and two rear pieces that are bent at both end portions of the element mounting portion and extend in a direction away from the element mounting portion. An internal space of the flexible wiring substrate surrounded by the element mounting portion and the two rear pieces is filled with adhesive resin in which a glass-transition temperature is 135° C. or less.

7 Claims, 7 Drawing Sheets

(51) Int. Cl.
  *A61M 25/00* (2006.01)
  *A61B 1/04* (2006.01)

(52) U.S. Cl.
  CPC ............. *A61B 1/051* (2013.01); *A61M 25/00* (2013.01); *A61B 1/00124* (2013.01); *A61B 1/04* (2013.01)

(58) Field of Classification Search
  CPC ............. A61B 1/00124; H04N 5/2251; H04N 5/2253; H04N 5/2254; H04N 5/2257
  USPC .................. 600/109, 110, 112, 132, 160, 178
  See application file for complete search history.

(56) References Cited

U.S. PATENT DOCUMENTS

| | | | | |
|---|---|---|---|---|
| 5,754,313 A | * | 5/1998 | Pelchy | A61B 1/042 348/65 |
| 2005/0216075 A1 | * | 9/2005 | Wang | A61L 29/18 623/1.15 |
| 2008/0117324 A1 | * | 5/2008 | Minamio | H04N 5/2253 348/340 |
| 2011/0135749 A1 | * | 6/2011 | Sellinger | C07F 7/21 424/601 |
| 2011/0249106 A1 | | 10/2011 | Makino et al. | |
| 2011/0301414 A1 | * | 12/2011 | Hotto | A61B 1/00009 600/114 |
| 2012/0197081 A1 | * | 8/2012 | Kimura | A61B 1/00124 600/110 |
| 2014/0009593 A1 | | 1/2014 | Segi et al. | |
| 2015/0228678 A1 | * | 8/2015 | Yoshida | A61B 1/00071 600/110 |
| 2016/0284754 A1 | * | 9/2016 | Takazawa | H01L 27/14634 |
| 2016/0301833 A1 | * | 10/2016 | Shimono | H04N 5/2253 |

FOREIGN PATENT DOCUMENTS

| | | |
|---|---|---|
| JP | 2011-217887 A | 11/2011 |
| JP | 2013-214815 A | 10/2013 |
| WO | 2013/147191 A1 | 10/2013 |

OTHER PUBLICATIONS

Specification for U.S. Appl. No. 15/055,924, filed Feb. 29, 2016.
Communication dated Mar. 8, 2016 from Japanese Patent Office in counterpart Application No. 2015-080227.

* cited by examiner

IMAGING MODULE AND CATHETER WITH FLEXIBLE WIRING SUBSTRATE

CROSS REFERENCE TO RELATED APPLICATIONS

Priority is claimed on Japanese Patent Application No. 2015-080227, filed on Apr. 9, 2015, the contents of which are incorporated herein by reference.

BACKGROUND OF THE INVENTION

Field of the Invention

The present invention relates to an imaging module in which a solid-state imaging element is connected to an electrical cable via a flexible wiring substrate, and a catheter configured using the imaging module.

Description of Related Art

A lot of imaging modules in which an imaging unit having a solid-state imaging element is assembled to the tip of an electrical cable are adopted for catheters.

The imaging modules have, for example, a configuration in which a flexible wiring substrate (FPC) having a solid-state imaging element mounted thereon and an objective lens unit are housed within a tubular metal frame member and the solid-state imaging element is electrically connected to an electrical cable via the flexible wiring substrate.

In an imaging element shown in Japanese Unexamined Patent Application, First Publication No. 201.1-217887, a flexible wiring board (FPC) having an imaging element chip (solid-state imaging element) mounted at a central portion thereof is electrically connected to a signal cable. The wiring board is bent to a side opposite to the imaging element chip at both ends in a location where the imaging element chip is mounted, and a block for supporting and guiding the wiring board is provided in a space surrounded by a central portion and an extension portion of the wiring board.

In an imaging module shown in Japanese Unexamined Patent Application, First Publication No. 2013-214815, a flexible wiring substrate (FPC) having a solid-state imaging element at a central portion thereof is connected to an electrical cable. The flexible wiring substrate is bent to a side opposite to the solid-state imaging element, and an internal space surrounded by the element mounting portion and a rear piece is filled with resin that supports the flexible wiring substrate.

In the imaging element shown in Japanese Unexamined Patent Application, First Publication No. 2011-217887, it is necessary to fix the extension portion of the wiring board to the block in order for it to be connected to the signal cable, and it is difficult to reduce the diameter thereof due to the presence of the block. For example, it is difficult to set the outside dimension of the imaging module portion to 2 mm or less. Additionally, there is concern that the wiring board may be disconnected due to warpage caused by a difference in coefficient of thermal expansion from that of the block.

In the imaging module shown in Japanese Unexamined Patent Application, First Publication No. 2013-214815, it is difficult to make a diameter small without causing disconnection in the bent portion of the flexible wiring substrate.

SUMMARY

The present invention has been made in view of the above-described circumstances, and provides an imaging module and a catheter that can make a diameter small without impairing connection reliability.

A first aspect of the present invention is an imaging module including an electrical cable; a solid-state imaging element having an imaging unit orthogonal to an axis direction of a tip of the electrical cable; and a flexible wiring substrate in which the solid-state imaging element and the electrical cables are electrically connected together. The flexible wiring substrate includes an element mounting portion mounting the solid-state imaging element, and two rear pieces that are bent at both end portions of the element mounting portion and extend in a direction moving away from the element mounting portion. An internal space of the flexible wiring substrate surrounded by the element mounting portion and the two rear pieces is filled with adhesive resin in which a glass-transition temperature is 135° C. or less.

In a second aspect of the present invention according to the imaging module of the first aspect described above, it is preferable that the rear pieces have extending portions configured so that portions, which include at least extending ends, approach each other as the extending portions are away from the element mounting portion, and connecting pieces further extending from the extending ends, and the internal space be surrounded by the element mounting portion and the extending portions.

In a third aspect of the present invention according to the imaging module of the first aspect or the second aspect described above, it is preferable that the outside dimensions of the flexible wiring substrate including the element mounting portion and the two rear pieces, which cover the adhesive resin, be equal to or less than the outside dimensions of the solid-state imaging element.

In a fourth aspect of the present invention according to the imaging module of any one of the first to the third aspects described above, it is preferable that the adhesive resin be an acrylic resin or an epoxy-based resin.

In a fifth aspect of the present invention according to the imaging module of the second aspect described above, it is preferable that the adhesive resin have intermediate corners between first, second corners, which are formed between the element mounting portion and the two extending portions, and a third corner formed in a place where the two extending portions meet, respectively, and be formed in a polygonal shape having five or more sides as a whole.

In a sixth aspect of the present invention according to the imaging module of any one of the first to the fifth aspects described above, it is preferable that a rate of volumetric shrinkage in curing of the adhesive resin be 3% or more.

A seventh aspect of the present invention is a catheter including an imaging module of any one of the first to the sixth aspects described above.

According to the aspects of the present invention described above, an internal space of the flexible wiring substrate surrounded by the element mounting portion and the two rear pieces is filled with adhesive resin in which a glass-transition temperature is 135° C. or less. Therefore, the adhesive resin can be softened when being put in a high-temperature state (for example, 135° C. or more) in sterilization processing using an autoclave. Accordingly, a situation in which a large force is applied to the bent portion or the like of the flexible wiring substrate can be avoided even in a high-temperature state, and damage of the flexible wiring substrate can be prevented. As a result, connection reliability can be improved.

According to the aspects of the present invention described above, since no large force is applied to the flexible wiring substrate by adhesive resin, an excessive force is not applied to the bent portion even if the outside dimensions of the flexible wiring substrate surrounding the adhesive resin are made small. Hence, the diameter of the imaging module can be reduced by adjusting the shape of the flexible wiring substrate surrounding the adhesive resin.

Additionally, according to the aspects of the present invention described above, since a configuration is provided in which the internal space of the flexible wiring substrate is filled with the adhesive resin, a member for maintaining the shape of the flexible wiring substrate is unnecessary, and disconnection of the flexible wiring substrate caused by a difference in coefficient of thermal expansion from that of the member does not occur.

DETAILED DESCRIPTION OF THE PREFERRED EMBODIMENTS

An embodiment of the present invention is described with reference to FIGS. 1 to 6E. In the following description, in FIG. 1, a left end portion, that is, a solid-state imaging element 4 side with respect to a flexible wiring substrate 10 is referred to as a front portion, and a right end portion opposite (right side in FIG. 1) to the left end portion is referred to as a rear portion. FIGS. 1 to 6E are views as seen from a direction perpendicular to a forward-rearward direction and a longitudinal direction D1 (to be described below).

Figure 1:
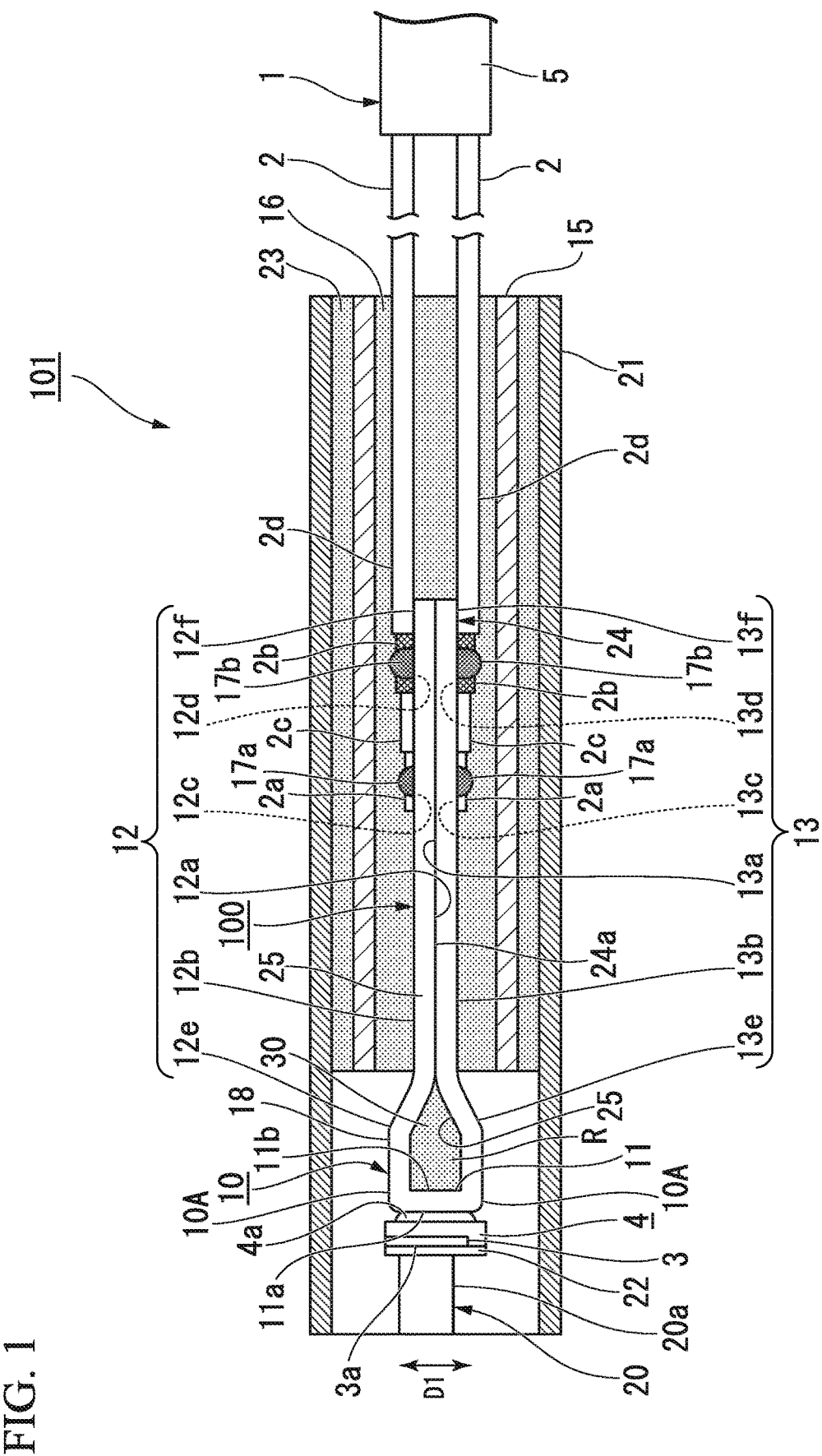
FIG. 1 is a sectional view showing an imaging module related to an embodiment of the present invention and a tip structure of a catheter assembled using the imaging module.
Figure 2A:
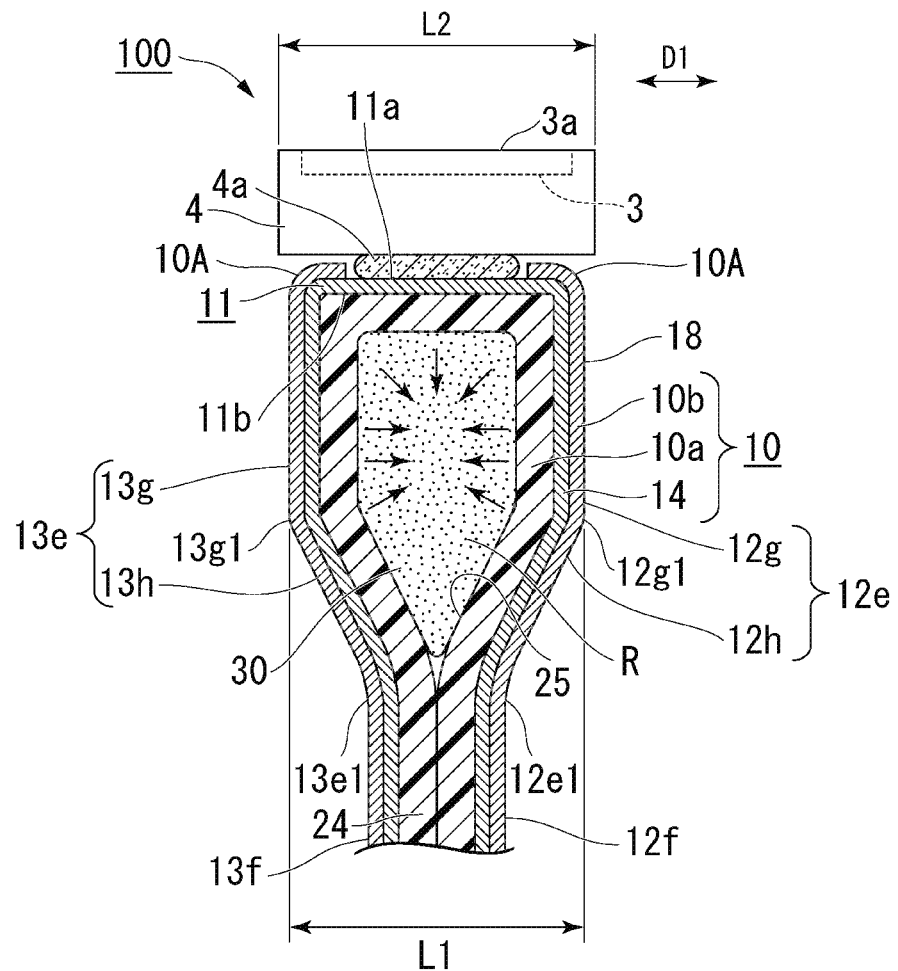
FIG. 2A is a sectional view showing a portion of a tip portion of the imaging module.
Figure 2B:
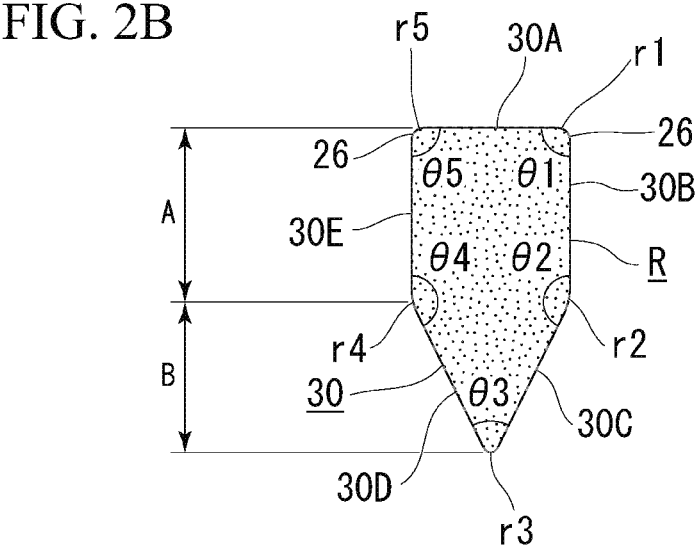
FIG. 2B is a view showing adhesive resin.

FIG. 1 shows an imaging module 100 of the embodiment related to the present invention and a tip structure of a catheter 101 assembled using the imaging module 100. FIG. 2A is a sectional view showing a portion of a tip portion of the imaging module, and FIG. 2B is a view showing an adhesive resin.

The imaging module 100 is configured by electrically connecting and attaching a flexible wiring substrate 10 (FPC), on which the solid-state imaging element 4 having an imaging unit 3 is mounted, to the tip of a conductor 2 of an electrical cable 1. As the solid-state imaging element 4, for example, a complementary metal oxide semiconductor (CMOS) can be suitably used.

The imaging module 100 is configured such that the solid-state imaging element 4 is electrically connected to the electrical cable 1 via the flexible wiring substrate 10.

The flexible wiring substrate 10, as shown in FIG. 2A, has an element mounting portion 11 in which the solid-state imaging element 4 is mounted on the front portion of a mounting surface 11a, and two rear pieces 12 and 13 that are bent at both end portions of the element mounting portion 11 and extends to the rear portion.

As the flexible wiring substrate 10 is bent at both the end portions of the element mounting portion 11 and is made to extend to the rear portion, the two rear pieces 12 and 13 are formed.

The flexible wiring substrate 10 is, for example, a single-sided wiring type flexible wiring substrate. That is, the flexible wiring substrate 10, as shown in FIG. 2A, has a structure in which wiring 14 formed on one surface side of an insulated base material 10a with electric insulation formed in the shape of a film is covered with a resist film 10b (a covering layer, for example, solder resist) with electrical insulation. The insulated base material 10a is made of, for example, polyimide, and the wiring 14 is made of, for example, copper.

A mounting part back surface 11b is a surface opposite to the mounting surface 11a of the element mounting portion 11.

As shown in FIG. 1, outside surfaces 12b and 13b (outer surface) of the rear pieces 12 and 13 are respectively provided with pad-like terminal portions 12c, 12d, 13c, and 13d for a conductor, An inner conductor 2a and an outer conductor 2b of the conductor 2 that is led out from a jacket 5 of the electrical cable 1 are electrically connected to the terminal portions 12c, 12d, 13c, and 13d for a conductor, respectively.

In electrical cable 1, a cable unit is configured by a plurality of the conductors 2 being collectively covered with the jacket 5.

The conductor 2 has the inner conductor 2a, a primary covering layer 2c that covers the inner conductor 2a, an outer conductor 2b that is formed in a net-like fashion of thin metallic wires and is provided around the primary covering layer 2c, and a secondary covering layer 2d that covers the outer conductor 2b.

As shown in FIGS. 1 and 2A, the imaging unit 3 is electrically connected to the wiring 14 of the flexible wiring substrate 10 via an electric circuit formed in the solid-state imaging element 4.

The solid-state imaging element 4 has a bump 4a, electrically connected the electric circuit of the solid-state imaging element 4, on a back surface thereof opposite to a surface on which the imaging unit 3 is mounted. The bump 4a is, for example, a solder bump, a stud bump, a plating bump, or the like.

The solid-state imaging element 4 is of a flip chip type, and is electrically connected to the wiring 14 of the flexible wiring substrate 10 by joining and fixing the bump 4a to an electrode portion (not shown) formed on the mounting surface 11a of the element mounting portion 11 of the flexible wiring substrate 10.

The element mounting portion 11 of the flexible w ng substrate 10 is electrically connected to the respective terminals 12c, 12d, 13c, and 13d which are for a conductor via the wiring 14 of the flexible wiring substrate 10. Accordingly, the electric circuit of the solid-state imaging element 4 and the conductor 2 of the electrical cable 1 are electrically connected together via the wiring 14.

The entire rear pieces 12 and 13 of the flexible wiring substrate 10 in the imaging module 100 are covered with an insulating tube 15 having electric insulation.

The insulating tube 15 is, for example, a tubular member made of silicone resin, and is suitable in that the insulating tube can be smoothly and slidingly moved at low friction with respect to the conductor 2 of the electrical cable 1 or the flexible wiring substrate 10.

The insulating tube 15 is fixed to and integrated with the internal flexible wiring substrate 10 and the conductor 2 with inner layer resin 16 that fills the inside of the insulating tube and is cured.

A conductor connecting portion 17a obtained by soldering the conductor 2a of the conductor 2 to the terminals 12c and 13c for a conductor and a conductor connecting portion 17b obtained by soldering the conductor 2b of the conductor 2 to the terminals 12d and 13d for a conductor are respectively formed in the rear pieces 12 and 13 of the flexible wiring substrate 10.

In the imaging module 100, the catheter 101 is configured by further mounting a lens unit 20 and an outer frame member 21

The lens unit 20 is attached to a light-receiving surface 3a of e imaging unit 3 via a transparent cover member 22.

The outer frame member 21 is a member having, for example, a cylindrical shape or the like, which houses a tip of the imaging module 100 together with the cover member 22 and the lens unit 20 that are fixed to the solid-state imaging element 4.

The lens unit 20 is obtained by incorporating an objective lens (not shown) into a cylindrical lens barrel 20a, and is provided by aligning an optical axis with the light-receiving surface 3a of the imaging unit 3 and fixing one end of the lens barrel 20a in an axis direction to the cover member 22.

The lens unit 20 focuses the light, which is guided via a lens within the lens barrel 20a from a front portion of an imaging tip unit 12, on the light-receiving surface 3a of the imaging unit 3 in the solid-state imaging element 4.

The outer frame member 21 is bonded and secured to the insulating tube 15 of the imaging module 100 with outer layer resin 23 that fills the inside of the outer frame member and is cured.

The insulating tube 15 prevents the conductor connecting portion 17a and the conductor connecting portion 17b, which are respectively formed in the two rear pieces 12 and 13 of the flexible wiring substrate 10, from contacting the outer frame member 21 to cause short-circuiting.

The flexible wiring substrate 10 of the imaging module 100 will be further described.

As shown in FIGS. 1 and 2A, the rear pieces 12 and 13 of the flexible wiring substrate 10 have extending portions 12e and 13e that are bent with respect to the element mounting portion 11, and connecting pieces 12f and 13f that extend from extending ends 12e1 and 13e1 of the extending portions 12e and 13e to the rear portion.

As shown in FIG. 2A, the extending portions 12e and 13e have extending base portions 12g and 13g and inclined extending portions 12h and 13h.

In FIG. 2A, the extending base portions 12g and 13g extend from both the end portions (both the end portions of the substrate in the longitudinal direction D1 (upward-downward direction in FIG. 1)) of the element mounting portion 11 to the rear portion. The extending base portions 12g and 13g are substantially perpendicular to the element mounting portion 11.

The inclined extending portions 12h and 13h extend from extending ends 12g1 and 13g1 of the extending base portions 12g and 13g so as to approach each other as inclined extending portions are separated from the element mounting portion 11. The inclined extending portions 12h and 13h abut against each other in the extending ends 12e1 and 13e1.

As shown in FIG. 1, the connecting piece portions 12f and 13f constitute a substrate mating portion 24 in which facing surfaces 12a and 13a are made to abut against each other.

In the substrate mating portion 24, the connecting pieces 12f and 13f are bonded together with interlayer resin 24a interposed between the facing surfaces 12a and 13a.

A substrate internal space 25, having a home base shape, which are surrounded by the extending portions 12e and 13e, the element mounting portion 11, and the substrate mating portion 24 is filled with adhesive resin R. The extending portions 12e and 13e and the element mounting portion 11 are bonded and secured to each other with the adhesive resin R.

In the flexible wiring substrate 10, the shape of a portion located around the substrate internal space 25 is constrained with the adhesive resin R that fills the substrate internal space 25 and is cured, and is not easily deformed, and shape stability is guaranteed.

That is, in the flexible wiring substrate 10, the shape of a tip portion 18 (a portion consisting of the element mounting portion 11 and the extending portions 12e and 13e) of the flexible wiring substrate 10 can be stably maintained with the adhesive resin R that is buried and cured in the substrate internal space 25.

It is preferable that the elastic modulus of the insulated base material 10a constituting the flexible wiring substrate 10 be 6 GPa or less, and it is preferable that the elastic modulus of the wiring 14 constituting the flexible wiring substrate 10 similar to the insulated base material 10a be 35 GPa or less.

Next, the substrate internal space 25 formed between the element mounting portion 11 and the rear pieces 12 and 13 of the flexible wiring substrate 10 and the adhesive resin R, which fills the substrate internal space 25, will be described below with reference to FIGS. 1 to 3.

As shown in FIGS. 1 to 2B, the adhesive resin R with which the substrate internal space 25 of the flexible wiring substrate 10 is filled is formed in a pentagonal shape (or a substantially pentagonal shape) (designated by reference sign 30) as a whole by the element mounting portion 11 and the rear pieces 12 and 13.

Figure 3:
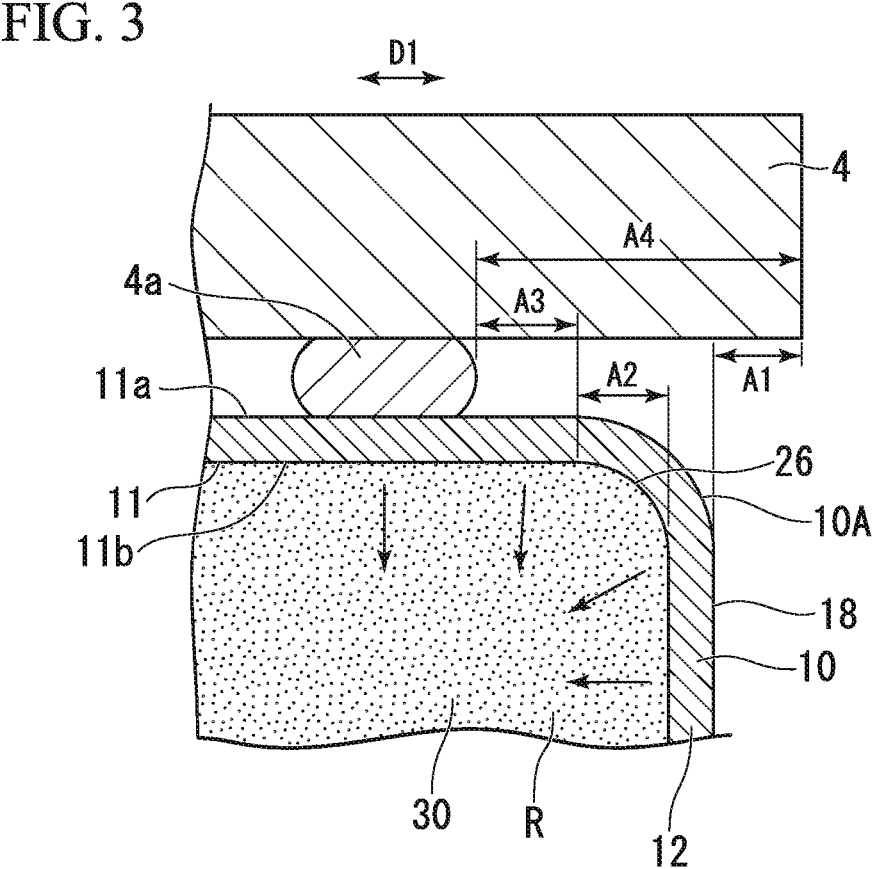
FIG. 3 is a view showing dimensions in the tip portion of the imaging module.

As shown in FIGS. 2A to 3, it is preferable that an outside dimension L1 of the flexible wiring substrate 10 surrounding the adhesive resin R be equal to or less than an outside dimension L2 of the solid-state imaging element 4 in the direction D1. It is preferable that the outside dimension L1 be smaller than the outside dimension L2. The outside dimensions L1 and L2 are the dimensions of the flexible wiring substrate 10 in the longitudinal direction D1 in the element mounting portion 11.

In FIG. 3, the outermost periphery (a right-end portion in FIG. 3) of the flexible wiring substrate 10 in the direction D1 is located on an inner side in the direction D1, compared to the outermost periphery (the right-end portion of FIG. 3) of the solid-state imaging element 4 in the direction D1.

It is preferable that the distance (designated by reference sign A1) in the direction D1 between the outermost periphery (the right-end portion of FIG. 3) of the flexible wiring substrate 10 in the direction D1 and the outermost periphery (the right-end portion of FIG. 3) of the solid-state imaging element 4 in the direction D1 be 0 mm to 0.195 mm.

It is preferable that an inside radius (designated by reference sign A2 in FIG. 3) of a bent portion 10A of the flexible wiring substrate 10 be 0.05 mm to 0.10 mm. By setting an inside radius A2 to this range, the diameter of the tip portion 18 can be made small, and disconnection in the bent portion 10A can be prevented.

It is, preferable that the distance (designated by reference sign A3 in FIG. 3) in the direction D1 from the outermost periphery (a right end of FIG. 3) of the bump 4a on the flexible wiring substrate 10 on which the solid-state imaging element 4 be mounted to the innermost periphery of the bent portion 10A in the direction D1 be 0 mm to 0.195 mm. By setting the distance A3 to this range, the diameter of the tip portion 18 can be made small.

It is preferable that the distance (designated by reference sign A4 in FIG. 3) in the direction D1 between the outermost periphery (the right end of FIG. 3) of the bump 4a on the flexible wiring substrate 10 on which the solid-state imaging element 4 is mounted and the outermost periphery (right-end portion of FIG. 3) of the solid-state imaging element 4 in the direction D1 be 0 mm to 0.195 mm. By setting the distance A4 to this range, the strength of joining between the element mounting portion 11 and the solid-state imaging element 4 can be enhanced.

When the internal diameter (designated by reference sign A2 in FIG. 3) of the bent portion 10A of the flexible wiring substrate 10 is set to be 0.05 mm to 0.10 mm, it is preferable to select a flexible material with an elastic modulus of 1.5 GPa or less and a breaking elongation of 30% or more for the resist film 10b (refer to FIG. 2A) located on an outside surface of the flexible wiring substrate 10. In addition, the elastic modulus of general resist for flexible wiring substrates is 3 GPa or more, and the breaking elongation is approximately several percents.

The reason why the inside bending radius of the bent portion 10A is 0.10 mm or less is because the bent portion 10A reaches the outer side beyond the outside dimensions of the solid-state imaging element 4 if the bending radius exceeds 0.10 mm.

Meanwhile, in the elastic modulus and the breaking elongation of the above-described general resist for flexible wiring substrates, there is a concern that the resist surface may break when the inside bending radius of the bent portion 10A is 0.10 mm or less.

Thus, breaking of a resist surface can be avoided by selecting materials with an elastic modulus of 1.5 GPa or less and a breaking elongation of 30% or more and setting the inside bending radius of the bent portion 10A to 0.05 mm or more in order to form the resist film 10b located on the outside surface of the flexible wiring substrate 10.

Additionally, if the inside bending radius of the bent portion 10A is less than 0.05 mm, breaking of the resist surface is apt to occur even if any kinds of material are used as a resist film 10b.

The resist film 10b for flexible wiring substrates is not an indispensable constituent element. The resist film may be omitted if necessary for prevention of an increase in the diameter of the flexible wiring substrate 10 as long as short circuiting does not occurs with respect to the outer frame member 21.

Figure 5:
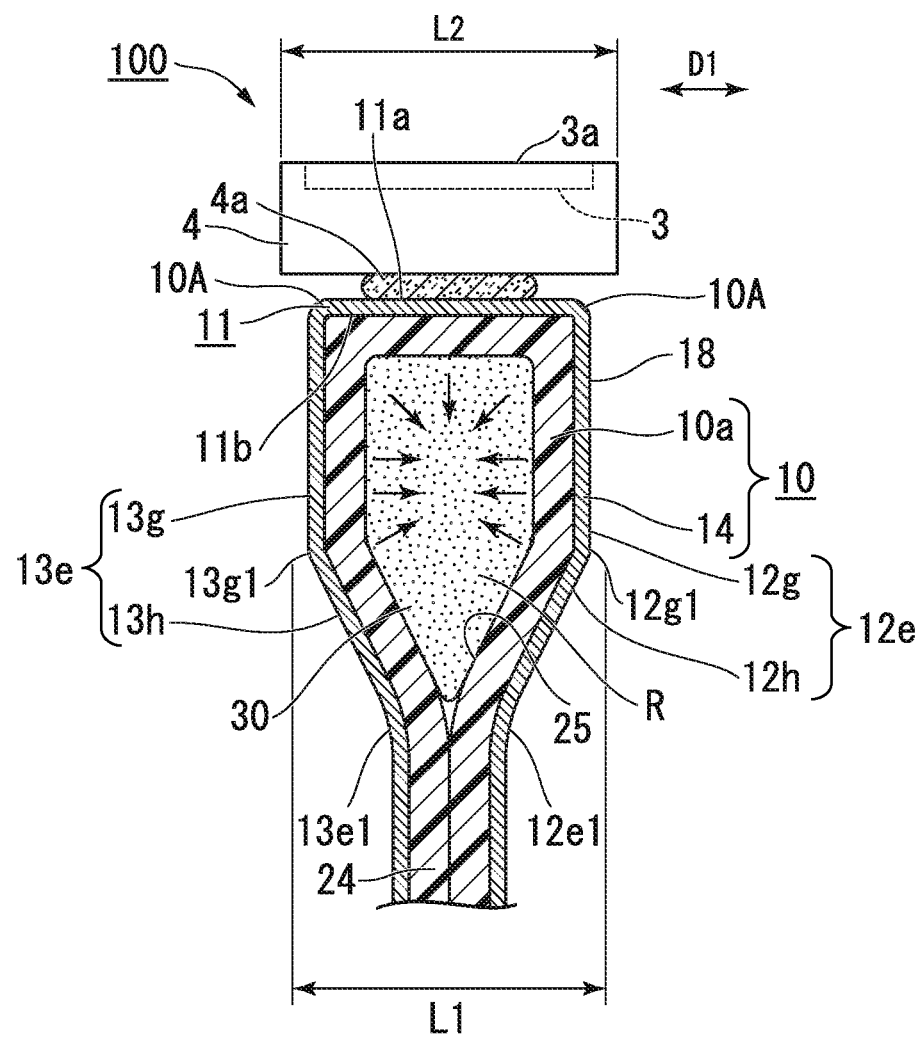
FIG. 5 is a sectional view showing a portion of a tip portion of another example of the imaging module.

FIG. 5 is a sectional view showing a portion of a tip portion of an imaging module in which the flexible wiring substrate 10 does not have the resist film 10b.

As shown in FIGS. 2A and 2B, the adhesive resin R with which the substrate internal space 25 of the flexible wiring substrate 10 is filled is formed in a pentagonal shape 30 having five corners (the angles of the respective corners are defined as θ1 to θ5) indicated by reference signs r1 to r5. Sides of the pentagonal shape 30 are respectively designated by reference signs 30A to 30E.

The corner r1 (first corner) and the corner r5 (second corner) of the adhesive resin R, as shown in FIGS. 2A and 2B, are corners between the element mounting portion 11 and the rear pieces 12 and 13. It is preferable that the angles θ1 and θ5 of the corners r1 and r5 be 90° or more. It is preferable that the corners r1 and r5 have a curved convex surface 26.

The corner r2 (intermediate corner) and the corner r4 (intermediate corner) are corners between the extending base portions 12g and 13g and the inclined extending portions 12h and 13h. It is preferable that the angles θ2 and θ4 of the corners r2 and r4 be 90° or more and less than 180°.

The corner r3 (third corner) is a corner formed in a place where the two inclined extending portions 12h and 13h are joined together.

In the shown example, the angles θ1 and θ5 of the corners r1 and r5 are approximately 90°, and the adhesive resin R forms a home base-like pentagonal shape 30 as a whole.

Figure 4A:
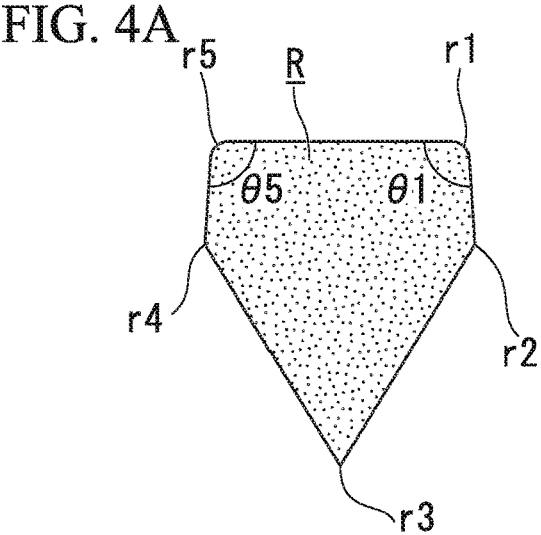
FIG. 4A shows a modification example of the adhesive resin with which the imaging module is filled, and shows an example in which angels θ1 and θ5 of corners r1 and r5 are made larger than 90°.
Figure 4B:
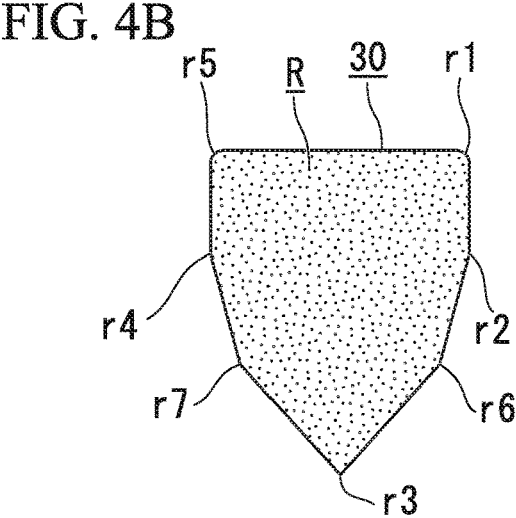
FIG. 4B shows a modification example of the adhesive resin with which the imaging module is filled, and shows an example in which the adhesive resin is a polygon of more than five sides.
Figure 4C:
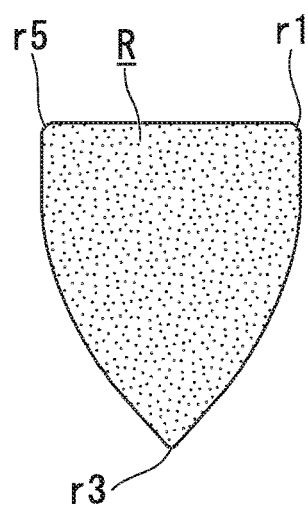
FIG. 4C shows a modification example of the adhesive resin with which the imaging module is filled, and shows an example in which the sides between corners r1 and r5 and a corner r3 of the adhesive resin are formed in a curved convex shape.

In addition, the shape of the adhesive resin R shown in FIGS. 1 to 2B is an example, and the shape of the adhesive resin R is not limited to this. For example, as shown in FIG. 4A, the angles θ1 and θ5 of the corners r1 and r5 may be larger than 90°. Additionally, as shown in FIG. 4B, the adhesive resin R may be formed in a polygonal shape exceeding a pentagonal shape. The adhesive resin R shown in FIG. 4B is a heptagon that has a corner r6 between the corner r2 and r3 and has a corner r7 between the corner r3 and r4. Additionally, as shown in FIG. 4C, a side between the corner r1 and the corner r3, and a side between the corner r5 and the corner r3 may be a curved convex shape.

Next, the adhesive resin R with which the substrate internal space 25 of the flexible wiring substrate 10 is filled will be described.

As the adhesive resin R, a resin in which a glass-transition temperature is 135° C. or less is used. As the adhesive resin R, for example, UV-curable acrylic resin or epoxy-based resin is suitably used. Accordingly, the adhesive resin R can be softened when the imaging module 100 is put in a high-temperature state (approximately 135° C. or more) in sterilization processing using an autoclave.

In addition to a glass transition temperature being 135° C. or less, materials for the adhesive resin R may also be selected taking a rate of volumetric shrinkage of the resin in curing into consideration.

For example, as the adhesive resin R, adhesive resin in which the rate of volumetric shrinkage is 3% or more is preferably used. Thus, in a manufacturing process to be described below, when a reference pin 50 is pulled out and the substrate internal space 25 is filled with the adhesive resin R and this adhesive resin is cured, the extending portions 12e and 13e are pulled inward with the shrinkage force of the adhesive resin R (refer to the arrow of FIG. 2A), so that the extending portions 12e and 13e can be inhibited from widening outward due to the restoring force of the flexible wiring substrate 10. Hence, the diameter of the tip portion 18 can be made smaller.

Since more contraction can be caused by the adhesive resin R if the rates of volumetric shrinkage are 5% or more and 10% or more, the diameter of the tip portion 18 can be made smaller.

In addition, as the UV-curable acrylic resin suitably used as the adhesive resin R, for example, there are those having properties in which the glass transition temperature is 106° C. and the rate of volumetric shrinkage in curing becomes 12.8%.

The imaging module 100 is manufactured, for example, as shown in FIGS. 6A to 6E.

Figure 6A:
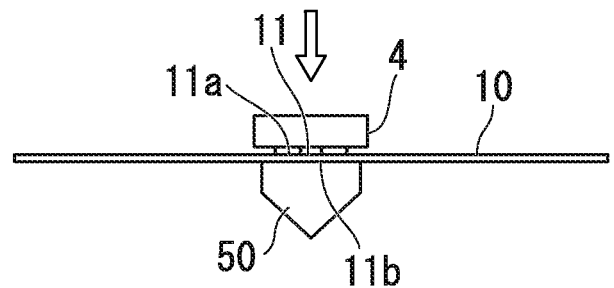
FIG. 6A is a view showing a process of manufacturing the imaging module of the present invention.

First, as shown in FIG. 6A, a pentagonal reference pin 50 is arranged on the mounting part back surface 11*b* of the flexible wiring substrate 10. The reference pin 50 brings a portion corresponding to a side 30A (refer to FIG. 2A) of the pentagonal shape 30 into close contact with the mounting part back surface 11*b* of the flexible wiring substrate 10.

The surface of the solid-state imaging element 4 installed on the mounting surface 11*a* of the flexible wiring substrate 10 is held down from above.

The outer shape of the reference pin 50 is appropriately selected to correspond to the shape of the adhesive resin R to be finally formed (refer to FIGS. 2A to 4C).

Figure 6B:
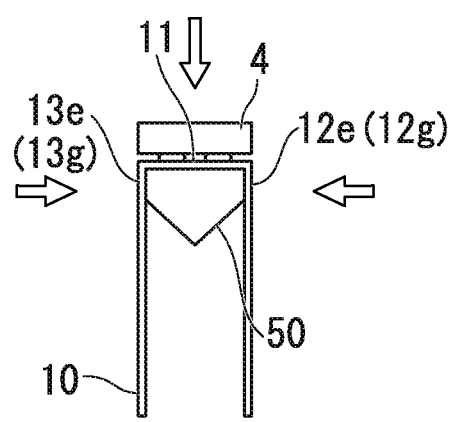
FIG. 6B is a view showing a process of manufacturing the imaging module of the present invention.

As shown in FIG. 6B, the extending portions 12*e* and 13*e* (extending base portions 12*g* and 13*g*) are formed by bending both the end portions of the element mounting portion 11 of the flexible wiring substrate 10.

Figure 6C:
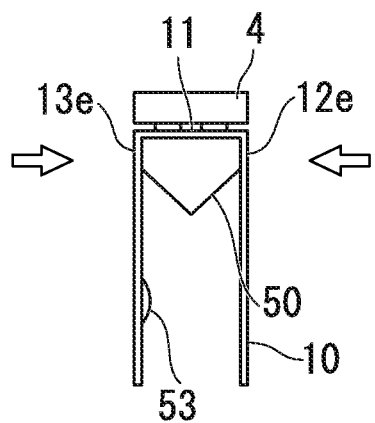
FIG. 6C is a view showing a process of manufacturing the imaging module of the present invention.

As shown in FIG. 6C, an adhesive 53 is coated on an inner surface of a location that becomes a connecting piece 13*f* of a rear piece 13 of the flexible wiring substrate 10.

Figure 6D:
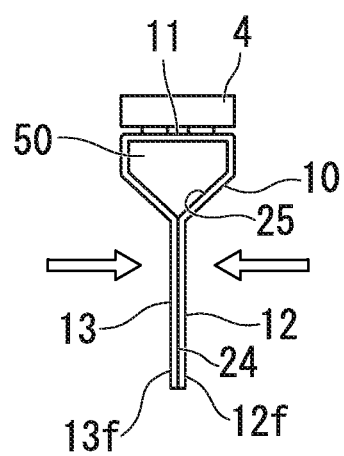
FIG. 6D is a view showing a process of manufacturing the imaging module of the present invention.

As shown in FIG. 6D, the connecting pieces 12*f* and 13*f* of the flexible wiring substrate 10 are bonded together with an adhesive 53. This forms the substrate mating portion 24 of the flexible wiring substrate 10.

Figure 6E:
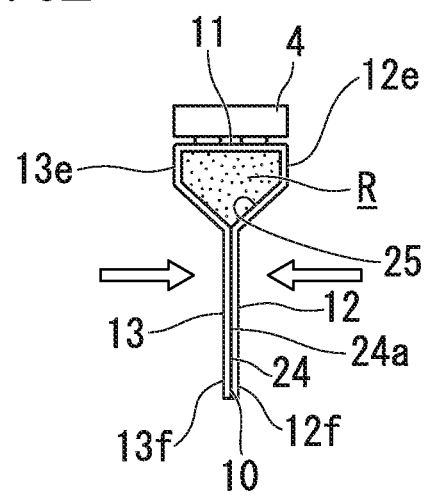
FIG. 6E is a view showing a process of manufacturing the imaging module of the present invention.

As shown in FIG. 6E, the adhesive resin R is cured after the reference pin 50 inserted between the element mounting portion 11 and the rear pieces 12 and 13 of the flexible wiring substrate 10 is pulled out and the substrate internal space 25 in which the reference pin 50 is arranged is filled with the adhesive resin. R.

In the imaging module 100, a substrate internal space 25 of the flexible wiring substrate 10 surrounded by the element mounting portion 11 and the two rear pieces 12, 13 is filled with adhesive resin R in which a glass-transition temperature is 135° C. or less. Therefore, the adhesive resin R can be softened when being put in a high-temperature state (for example, 135° C. or more) in sterilization processing using an autoclave.

Accordingly, a situation in which a large force is applied to the bent portion 10A or the like of the flexible wiring substrate 10 can be avoided even in a high-temperature state, and damage of the flexible wiring substrate 10 can be prevented. As a result, connection reliability can be improved.

Additionally, since no large force is applied to the flexible wiring substrate 10 by the adhesive resin R, an excessive force is not applied to the bent portion 10A even if the outside dimensions of the flexible wiring substrate 10 surrounding the adhesive resin R are made small. Hence, the diameter of the imaging module 100 can be reduced by adjusting the shape of the flexible wiring substrate 10 surrounding the adhesive resin R.

Since the imaging module 100 has a configuration in which the substrate internal space 25 of the flexible wiring substrate 10 is filled with the adhesive resin R, a member for maintaining the shape of the flexible wiring substrate 10 is unnecessary, and disconnection of the flexible wiring substrate 10 caused by a difference in coefficient of thermal expansion from that of the member does not occur.

In the imaging module 100, since the adhesive resin R which is softened in a high-temperature state is used, the adhesive resin R has a shape according to the shape of the flexible wiring substrate 10. Therefore, the alignment between the adhesive resin R and the flexible wiring substrate 10 is not necessary, and manufacture is easy.

In contrast, when the member for maintaining the shape of the flexible wiring, substrate 10 is used, since the alignment between the member and the flexible wiring substrate is required, substantial time and effort are required for manufacture. Additionally, since the member requires precision processing, high-volume manufacture is difficult, and costs increase.

Although the embodiment of the present invention has been described above in detail with reference to the drawings, the specific configuration is not limited to the embodiment, and design changes or the like are also included without departing from the scope of the present invention. For example, the extending portions are not limited to the shown structure as long as they have the structure in which portions including at least the extending ends approach each other as they move away from the element mounting portion.

Moreover, additions, omissions, substitutions, and other modifications can be made without departing from the spirit or scope of the present invention. Accordingly, the invention is not to be considered as being limited by the foregoing description, and is only limited by the scope of the appended claims.

What is claimed is:
1. An imaging module comprising:
an electrical cable;
a solid-state imaging element comprising an imaging unit orthogonal to an axis direction of a tip of the electrical cable; and
a flexible wiring substrate in which the solid-state imaging element and the electrical cable are electrically connected together,
wherein the flexible wiring substrate comprises an element mounting portion mounting the solid-state imaging element, a first rear piece that is bent at a first end of the element mounting portion and extends in a direction away from the element mounting portion, and a second rear piece that is bent at a second end opposite to the first end and extends in a direction away from the element mounting portion,
wherein the first rear piece comprises a first extending base portion, which extends directly from the first end and is perpendicular to the element mounting portion that extends from the first extending base portion, and a first inclined extending portion, and the second rear piece comprises a second extending base portion, which extends directly from the second end and is perpendicular to the element mounting portion, and a second inclined extending portion that extends from the second extending base portion,
wherein the first inclined extending portion and the second inclined extending portion are configured so that portions, which comprise at least a first extending end of the first inclined extending portion and the second extending end of the second inclined extending portion, approach each other as the first and second inclined extending portions are away from the element mounting portion, and wherein an internal space of the flexible wiring substrate surrounded by the element mounting portion, the first extending base portion, the first inclined extending portion, the second extending base portion, and the second inclined extending portion is filled with an adhesive resin in which a glass-transition temperature is 135° C. or less.

2. The imaging module according to claim 1, wherein the first and second rear pieces further comprise connecting pieces further extending from ones of the first extending end and the second extending end.

3. The imaging module according to claim 1, wherein the outside dimensions of the flexible wiring substrate comprising the element mounting portion and the first and second rear pieces, which cover the adhesive resin, are equal to or less than the outside dimensions of the solid-state imaging element.

4. The imaging module according to claim 1, wherein the adhesive resin is an acrylic resin or an epoxy-based resin.

5. The imaging module according to claim 1, wherein the adhesive resin has intermediate corners between first, second corners, which are formed between the element mounting portion and the two extending base portions, and a third corner formed in a place where the two inclined extending portions meet, respectively, and is formed in a polygonal shape having five or more sides as a whole.

6. The imaging module according to claim 1, wherein a rate of volumetric shrinkage in curing of the adhesive resin is 3% or more.

7. A catheter comprising: the imaging module according to claim 1.

* * * * *